United States Patent [19]
Lindel et al.

[11] Patent Number: 4,880,840
[45] Date of Patent: Nov. 14, 1989

[54] ARYLETHANOLHYDROXYLAMINES AND THEIR USE FOR PROMOTING YIELD

[75] Inventors: Hans Lindel, Leverkusen; Axel Ingendoh, Odenthal; Friedrich Berschauer, Wuppertal; Anno de Jong; Martin Scheer, both of Wuppertal, all of Fed. Rep. of Germany

[73] Assignee: Bayer Aktiengesellschaft, Leverkusen, Fed. Rep. of Germany

[21] Appl. No.: 68,398

[22] Filed: Jun. 30, 1987

[30] Foreign Application Priority Data

Jul. 16, 1986 [DE] Fed. Rep. of Germany ....... 3623940

[51] Int. Cl.⁴ ..................... A61K 31/135; C07C 83/04
[52] U.S. Cl. .................................... 514/645; 514/452; 514/466; 514/524; 514/539; 514/555; 514/597; 514/605; 514/620; 514/630; 549/262; 549/443; 558/422; 560/42; 564/51; 564/99; 564/165; 564/220; 564/300
[58] Field of Search ................. 564/363, 368, 51, 99, 564/165, 220, 300; 574/683; 260/501.18; 549/262, 443; 558/422; 560/42; 514/452, 466, 524, 539, 555, 597, 605, 620, 630, 645

[56] References Cited

U.S. PATENT DOCUMENTS

| | | | |
|---|---|---|---|
| 3,118,933 | 1/1964 | Goldberg et al. | 564/300 X |
| 3,173,953 | 3/1965 | McWhorter, Jr. | 260/583 |
| 3,184,510 | 5/1965 | Levy | 564/300 |
| 3,358,026 | 12/1967 | Schroter et al. | 564/300 |
| 3,637,854 | 1/1972 | Kyburz et al. | 564/300 |
| 4,382,958 | 5/1983 | Duckworth | 564/653 |
| 4,540,806 | 9/1985 | Freed et al. | 564/300 X |
| 4,588,749 | 5/1986 | Ferris | 564/363 X |
| 4,690,951 | 9/1987 | Anderson et al. | 514/653 |

FOREIGN PATENT DOCUMENTS

| | | |
|---|---|---|
| 23385 | 2/1981 | European Pat. Off. |
| 26298 | 4/1981 | European Pat. Off. |
| 0117647 | 9/1984 | European Pat. Off. |
| 0209025 | 1/1987 | European Pat. Off. |
| 2180234 | 3/1987 | United Kingdom |

OTHER PUBLICATIONS

Chem. Abst. Soc. 79 (1957), 6562.
R. Borch. J. Am. Chem. Soc. 93, 2897 (1971).
Baldwin et al., "Total Synthesis of Antitumor Agent at $-125$...", Tetrahedron, vol. 41, pp. 5241–5260, 1983.

Primary Examiner—Richard L. Raymond
Attorney, Agent, or Firm—Sprung, Horn, Kramer & Woods

[57] ABSTRACT

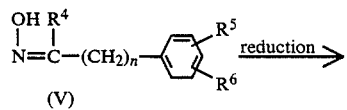

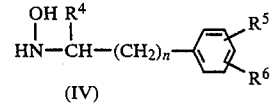

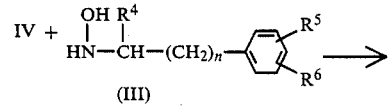

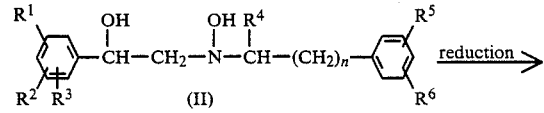

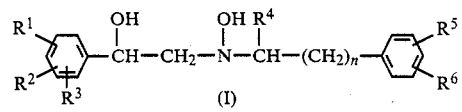

wherein $R^1$–$R^8$ and n are as defined herein.

13 Claims, No Drawings

ARYLETHANOLHYDROXYLAMINES AND THEIR USE FOR PROMOTING YIELD

The present invention relates to arylethanolhydroxylamines, processes for their preparation and their use as yield promoters for animals.

Arylethanolamines are known compounds. They have various pharmacological properties, depending on their chemical structure. Inter alia, certain arylethanolamines have effects on the weight increase of animals and on the ratio of meat to fat (EP-OS (European Published Specification) No. 26,298). The basic structure of the arylethanolamine also appears to be of decisive importance for the action.

1. The new arylethanolhydroxylamines of the formula I

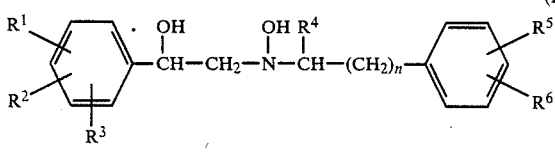

in which $R^1$ represents halogen, CN, $NO_2$, hyroxyl or optionally substituted alkyl, alkoxy or alkylthio, or furthermore represents alkoxycarbonyl or the radical $-NR^7R^8$, $R^2$ represents hydrogen, halogen, CN, hydroxyl or optionally substituted alkoxy, it being possible for the radicals $R^1$ and $R^2$, together with the adjacent C atoms, to form an optionally substituted dioxolanyl or dioxanyl ring, $R^3$ represents hydrogen or halogen, $R^4$ represents hydrogen or alkyl, $R^5$ represents hydrogen, optionally substituted alkyl or alkoxy, hydroxyl or halogen, $R^6$ represents acyl, acyloxy or alkoxy, which is optionally substituted, $R^7$ represents hydrogen or alkyl, $R^8$ represents hydrogen, or alkyl, formyl (—CHO), acyl or optionally substituted aryl or aralkyl and n represents 0, 1 or 2, and physiologically acceptable salts, enantiomers and diastereomers thereof, have been found.

2. A process has been found for the preparation of the arylethanolhydroxylamines of the formula I

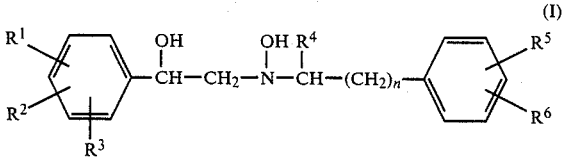

in which $R^1$ represents halogen, CN, $NO_2$, hydroxyl or optionally substituted alkyl, alkoxy or alkylthio, or furthermore represents alkoxycarbonyl or the radical $-NR^7R^8$, $R^2$ represents hydrogen, halogen, CN, hydroxyl or optionally substituted alkoxy, it being possible for the radicals $R^1$ and $R^2$, together with the adjacent C atoms, to form an optionally substituted dioxolanyl or dioxanyl ring, $R^3$ represents hydrogen or halogen, $R^4$ represents hydrogen or alkyl, $R^5$ represents hydrogen, optionally substituted alkyl or alkoxy, hydroxyl or halogen, $R^6$ represents acyl, acyloxy or alkoxy, which is optionally substituted, $R^7$ represents hydrogen or alkyl, $R^8$ represents hydrogen, alkyl, formyl (—CHO), acyl or optionally substituted aryl or aralkyl and n represents 0, 1 or 2, which is characterized in that arylglyoxalnitrones of the formula II

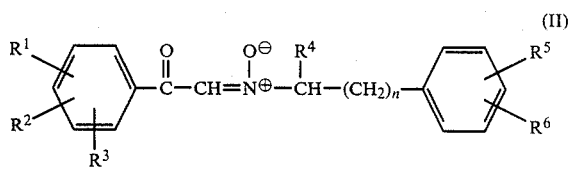

in which $R^1$, $R^2$, $R^3$, $R^4$, $R^5$, $R^6$ and n have the abovementioned meaning, are reduced.

3. The new arylglyoxalnitrones of the formula II

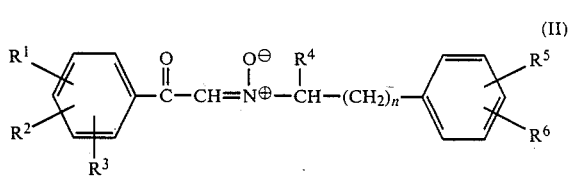

in which $R^1$ represents halogen, CN, $NO_2$, hydroxyl or optionally substituted alkyl, alkoxy or alkylthio, or furthermore represents alkoxycarbonyl or the radical $-NR^7R^8$, $R^2$ represents hydrogen, halogen, CN, hydroxyl or optionally substituted alkoxy, it being possible for the radicals $R^1$ and $R^2$, together with the adjacent C atoms, to form an optionally substituted dioxolanyl or dioxanyl ring, $R^3$ represents hydrogen or halogen, $R^4$ represents hydrogen or alkyl, $R^5$ represents hydrogen, optionally substituted alkyl or alkoxy, hydroxyl or halogen, $R^6$ represents acyl, acyloxy or alkoxy, which is optionally substituted, $R^7$ represents hydrogen or alkyl, $R^8$ represents hydrogen, alkyl, formyl (—CHO), acyl or optionally substituted aryl or aralkyl and n represents 0, 1 or 2, have been found.

4. A process has been found for the preparation of the new arylglyoxalnitrones of the formula II

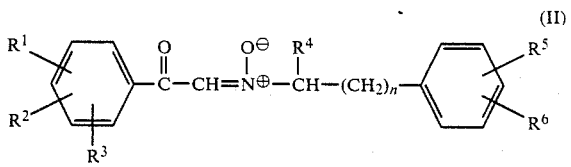

in which $R^1$, $R^2$, $R^3$, $R^4$, $R^5$, $R^6$ and n have the meaning given in 3 (above), which is characterized in that arylglyoxals of the formula III

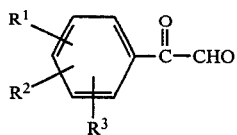

in which $R^1$, $R^2$ and $R^3$ have the abovementioned meaning, if appropriate in the form of their hydrates or adducts with alcohols, are reacted with hydroxylamines of the formula IV

in which $R^4$, $R^5$, $R^6$ and n have the abovementioned meaning, water being split off.

5. The new hydroxylamines of the formula IV

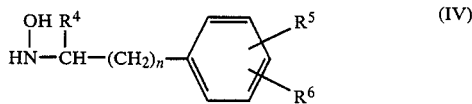

in which $R^4$, $R^5$, $R^6$ and n have the meaning given in 3 (above), have been found.

6. A process has been found for the preparation of the new hydroxylamines of the formula IV

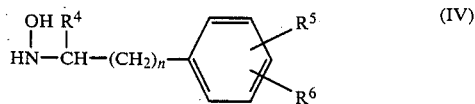

in which $R^4$, $R^5$, $R^{6'}$ and n have the abovementioned meaning, which is characterized in that oximes of the formula V

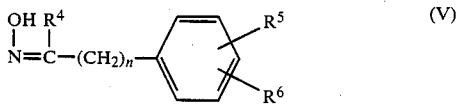

in which $R^4$, $R^5$, $R^6$ and n have the abovementioned meaning, are reduced.

The arylethanolhydroxylamines exhibit an outstanding yield-increasing action on animals. They can therefore be used as yield promoters in the field of animal nutrition. This property was surprising. In fact, it was known of arylethanolamines that changes in the substitution of the amine portion of the molecule lead to marked changes in the biological and pharmacologial action. It was therefore in no way to be expected that a completely different chemical class of compounds, that is to say hydroxylamines, have economically useful actions.

Preferred compounds of the formula I are those in which $R^1$ represents fluorine, chlorine, bromine, CN, nitro, hydroxyl, $C_{1-4}$-alkyl, $C_{1-4}$-halogenoalkyl, $C_{1-4}$-hydroxyalkyl, $C_{1-4}$-alkoxyalkyl, $C_{1-4}$-alkoxy, $C_{1-4}$-halogenoalkoxy, benzyloxy, $C_{1-4}$-alkylthio, $C_{1-4}$-halogenoalkylthio, $C_{1-4}$-alkoxycarbonyl, $C_{1-4}$-alkylsulphonylmethyl or the radical $-NR^7R^8$, $R^2$ represents hydrogen, fluorine, chlorine, bromine, CN, hydroxyl or $C_{1-4}$-alkoxy, it being possible for the radicals $R^1$ and $R^2$, together with the C atom to which they are bonded, to form a dioxolanyl or dioxanyl ring which is optionally substituted by fluorine or chlorine, $R^3$ represents hydrogen, fluorine, chlorine or bromine, $R^4$ represents hydrogen or $C_{1-3}$-alkyl, $R^5$ represents hydrogen, or hydroxyl, fluorine, chlorine, bromine or $C_{1-10}$-alkyl, which is optionally substituted by halogen, OH, CN or phenyl, or represents $C_{1-4}$-alkoxy, $R^6$ represents $C_{1-3}$-alkoxy, which is optionally substituted by OH, halogen, $C_{1-2}$-alkoxy, $-COR^9$ or $-CONR^7R^8$, or represents one of the following radicals: $-COR^9$, $-SO_2R^{10}$, $-CONR^7R^8$ or $-O-COR^9$, $R^7$ represents hydrogen, $C_{1-4}$-alkyl, optionally substituted benzyl or phenyl, $R^8$ represents hydrogen, $C_{1-4}$-alkyl, $-CHO$, $-COR^9$, $-CONH_2$, $-CONH(C_{1-4}$-alkyl$)$, $-CON(C_{1-4}$-alkyl$)_2$ or $-SO_2-(C_{1-4}$-alkyl$)$, $R^9$ represents hydroxyl, $C_{1-4}$-alkoxy, $C_{1-4}$-alkyl or optionally substituted phenyl and $R^{10}$ represents $C_{1-4}$-alkyl or $C_{1-4}$-halogenoalkyl.

Particularly preferred compounds of the formula I are those in which $R^1$ represents chlorine, bromine, CN, OH, nitro, methyl, hydroxymethyl, methyl, methoxy, methylsulphonylmethyl, trifluoromethyl, amino, formamido, acetamido, methylsulphonamido, ureido or methoxybenzylamino, $R^2$ represents hydrogen, chlorine, bromine, CN, hydroxyl or methoxy, $R^3$ represents hydrogen, chlorine, or bromine, $R^4$ represents hydrogen or methyl, $R^5$ represents hydrogen or methoxy or ethoxy, which are not optionally substituted by OH, $R^6$ represents methoxy or ethoxy, which are optionally substituted by OH, or represents $-COR^9$ or $-O-CH_2-COR^9$, $R^9$ represents $C_{1-4}$-alkyl or $C_{1-4}$-alkoxy, in particular methoxy, ethoxy or isopropoxy, and n represents 1.

Compounds of the formula I which may be mentioned in particular are those in which $R^1$ represents chlorine, bromine, CN, OH, methylsulphonylmethyl, hydroxyl, methoxy or amino, $R^2$ represents hydrogen, chlorine, CN, hydroxyl or methoxy, $R^3$ represents hydrogen or chlorine, $R^4$ represents methyl, $R^5$ represents hydrogen, $R^6$ represents methoxy, hydroxyethyl or $-COR^9$ or $-O-CH_2COR^9$, $R^9$ represents methoxy or isopropoxy and n represents 1.

The following compounds of the formula I may be mentioned specifically, in addition to the compounds mentioned in the examples:

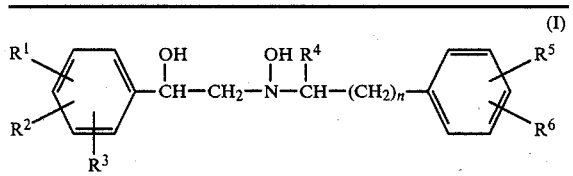

| $R^1$ | $R^2$ | $R^3$ | $R^4$ | n | $R^5$ | $R^6$ |
|---|---|---|---|---|---|---|
| 2-Br | H | H | $CH_3$ | 1 | H | 4-$COOCH_3$ |
| 3-Cl | 4-Cl | H | H | 2 | 3-Cl | 4-COOH |
| 3-$CH_3O$ | 4-$CH_3O$ | H | $CH_3$ | 2 | H | 4-$OCH_2COOCH_3$ |
| 4-$NH_2$ | 3-CN | H | $CH_3$ | 1 | H | 4-$OCH_2COOCH_3$ |

The compounds of the formula I can also exist in the form of their steric and optical isomers and thereby result in forms which are enantiomeric and/or diastereomeric to one another.

Physiologically acceptable salts of the compounds of the formula I can be formed with the following acids: hydrochloric acid, sulphuric acid, phosphoric acid, perchloric acid, hydrobromic, hydroiodic and hydrofluoric acid, nitric acid, acetic acid, oxalic acid, malonic acid, succinic acid, ascorbic acid, malic acid, tartaric acid, maleic acid, fumaric acid, methanesulphonic acid, benzoic acid, substituted benzoic acid, formic acid, chloroacetic acid, toluenesulphonic acid, benzenesulphonic acid, trichloroacetic acid, phthalic acid, naphthalenesulphonic acid and nicotinic acid.

The compounds of the formula I are obtained by reducing arylglyoxalnitrones of the formula II. The reaction can be represented by the following equation:

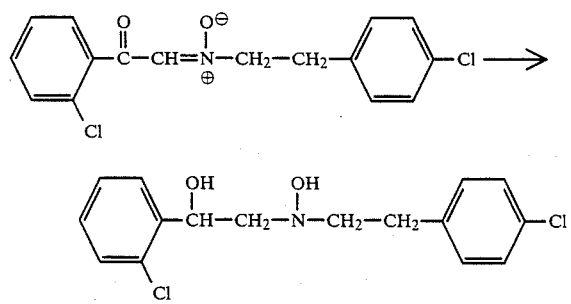

The arylglyoxalnitrones of the formula II in which the radicals $R^1$ to $R^6$ and n have the preferred meanings given in the case of the compound of the formula I are preferably employed.

The reduction is preferably carried out with complex hydrides, for example alkali metal borohydrides, such as, for example, $NaBH_4$, $NaBH_3CN$, $LiBH_4$ and $NaBH_x(O\text{-alkyl})_{4-x}$. $NaBH_4$ is particularly preferred here.

The reaction is preferably carried out in diluents. These include all the inert organic solvents. These include, in particular, aliphatic and aromatic optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore ethers, such as diglycol dimethyl ether, tetrahydrofuran and dioxane, and moreover alcohols, such as methanol, ethanol, isopropanol or higher-chain alcohols, and also esters, such as methyl and ethyl acetate, and furthermore nitriles, such as, for example, acetonitrile, propionitrile, benzonitrile and glutaric acid dinitrile, and moreover amides, such as, for example, dimethylformamide, dimethylacetamide and N-methylpyrrolidone, as well as dimethylsulphoxide, tetramethylene sulphone and hexamethylphosphoric acid triamide.

The reaction is carried out at temperatures of $-50°$ to $100°$ C., preferably at temperatures between $0°$ C. and $50°$ C.

Working up is carried out in the customary manner.

Arylglyoxalnitrones of the formula II are new. They are obtained by reacting arylglyoxals of the formula III with hydroxylamines of the formula IV. The reaction can be represented by the following equation:

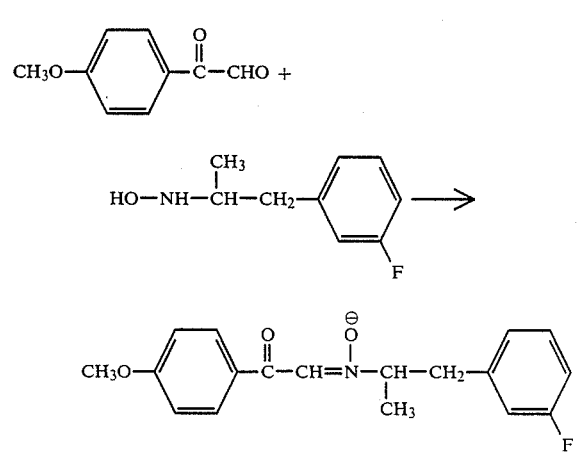

Arylglyoxals of the formula III are known or can be prepared by processes which are known per se (N. Kornblum et al., J. Am. Chem. Soc. 79 (1957), 6562), for example by oxidizing the corresponding α-halogenoacetophenones with, for example, dimethylsulphoxide, or oxidizing the corresponding acetophenones with selenium dioxide.

Arylglyoxals of the formula III in which the radicals $R^1$, $R^2$ and $R^3$ have the preferred meanings given in the case of compounds of the formula I are preferably used.

The following arylglyoxals may be mentioned specifically: 2-chlorophenylglyoxal, 3-chlorophenylglyoxal, 3-bromophenylglyoxal, 3-methylsulphonylmethyl-4-hydroxyphenylglyoxal, 3,4-dimethoxyphenylglyoxal and 3,5-dimethoxyphenylglyoxal.

Hydroxylamines of the formula IV are new. Their preparation is described below.

The reaction can be carried out with or without a diluent. Diluents which may be mentioned are: all the inert organic solvents. These include, in particular, aliphatic and aromatic optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, alcohols, such as methanol, ethanol, isopropanol, glycol and higher-chain alcohols, and furthermore ethers, such as diethyl ether, dibutyl ether, glycol dimethyl ether, diglycol dimethyl ether, tetrahydrofuran and dioxane, and moreover ketones, such as acetone, methyl ethyl ketone, methyl isopropyl ketone and methyl isobutyl ketone, and also esters, such as methyl and ethyl acetate, and furthermore nitriles, such as, for example, acetonitrile, propionitrile, benzonitrile and glutaric acid dinitrile, and moreover amides, such as, for example, dimethylformamide and N-methylpyrrolidone, as well as dimethylsulphoxide, tetramethylene sulphone and hexamethyl phosphoric acid triamide.

The N-alkylhydroxylamine of the general formula IV is preferably reacted as the salt of an inorganic or organic acid with the arylglyoxal of the general formula III in the presence of an alkali metal salt of a weak organic acid, such as, for example, sodium acetate.

The reaction can be carried out at temperatures of 10°–200° C., preferably 50°–150° C. and especially preferably at the boiling point of the solvent.

It is preferably carried out in the presence of a dehydrating agent. Examples of these which may be mentioned are $Na_2SO_4$, $MgSO_4$, $K_2CO_3$, $CaCl_2$, molecular sieves, silica gel and aluminum hydroxides. The water formed during the reaction can also be removed azeotropically from the reaction mixture.

The compounds of the formulae III and IV are preferably employed in the equimolar ratio.

Working up is carried out in a manner which is known per se.

In the preparation of arylethanol hydroxylamines of the general formula I, it is not necessary for the arylglyoxalnitrone of the general formula II to be isolated in all cases. It may prove to be particularly advantageous to carry out the reaction sequence in a one-pot reaction.

Hydroxylamines of the formula IV are new.

They can be prepared by reducing oximes of the formula V, for example with $NaBH_3CN$. The reaction can be represented by the following equation:

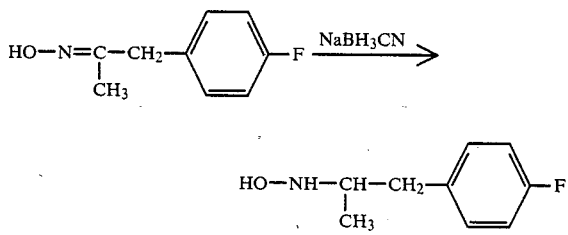

Oximes of the formula V are known (compare, for example, EP-OS (European Published Specfication) No. 23,385), or they can be prepared by processes analogous to known processes. The oximes of the formula V in which the radicals $R^4$ to $R^6$ and n have the preferred meanings given in the case of the compounds of the formula I are preferably used.

The reaction is carried out by introducing the reducing agent in portions into a solution of the oxime of the formula V in a suitable diluent and keeping the pH value of the reaction medium in the weakly acid range by simultaneous additions of an acid.

The reaction is carried out at −20° to +100° C., preferably at 20° C.

The reaction is carried out under normal pressure.

The starting components are employed in an approximately equimolar ratio.

The reaction is carried out in diluents. Diluents which may be mentioned are: alcohols, such as methanol, ethanol, isopropanol and ethylene glycol. The reaction can also be carried out in aqueous alcohols.

The reaction is carried out at a pH value of the reaction solution of about 1–4. The pH value can be determined by a calibrated glass electrode. The addition of a color indicator, such as bromocresol green or methyl orange, is also suitable for establishing the pH value.

Working up can be carried out in a manner which is known per se by acidifying the mixture with concentrated acid, such as hydrochloric acid, to decompose the cyanoborohydride and then rendering the mixture alkaline, followed by extraction of the N-alkylhydroxylamine with organic solvents (compare R. Borch J. Am. Chem. Soc. 93, 2897 (1971)).

It is particularly advantageous, however, after the borohydride reduction has ended and the borohydride has been decomposed with concentrated acid, such as hydrochloric acid, for the mixture to be concentrated under a waterpump vacuum and the residue to be extracted with chloroform, methylene chloride or alcohols, such as ethanol, isopropanol or methanol. The organic solution of the N-alkylhydroxylamine hydrochloride is dried with sodium sulphate or other suitable drying agents and concentrated on a rotary evaporator.

The compounds of the formula IV can also be prepared in a manner which is known per se by reduction of the corresponding nitro compounds with hydrogen under catalysis by, for example, palladium-on-charcoal (compare U.S. Pat. No. 3,173,953) or by reduction with zinc dust in glacial acetic acid, with aluminum amalgam or with tin-(II) chloride (compare Houben-Weyl, Methoden der org. Chemie (Methods of Organic Chemistry) Volume 10/1 page 1153).

The active compounds are used as yield promoters on animals for promoting and accelerating growth and milk and wool production and for improving the feed utilization and quality of the meat and for shifting the meat/fat ratio in favor of meat. The active compounds are used on stock animals, breeding animals, ornamental animals and hobby animals.

The stock and breeding animals include mammals, such as, for example, cattle, pigs, horses, sheep, goats, rabbits, hares and deer, fur-bearing animals, such as mink and chinchilla, poultry, such as, for example, chicken, geese, ducks, turkeys and pigeons, fish, such as, for example, carp, trout, salmon, eels, tench and pike, and reptiles, such as, for example, snakes and crocodiles.

The ornamental and hobby animals include mammals, such as dogs and cats, birds, such as parrots and canaries, and fish, such as ornamental and aquarium fish, for example goldfish.

The active compounds are used during all the growth and yield phases of the animals, regardless of the sex of the animals. The active compounds are preferably used during the intensive growth and yield phase. The intensive growth and yield phase lasts from one month to 10 years, depending on the species of animal.

The amount of the active compounds administered to the animals to achieve the desired effect can vary widely because of the favorable properties of the active compounds. It is preferably about 0.001 to 50 mg/kg, in particular 0.01 to 5 mg/kg of body weight per day. The appropriate amount of the active compound and the appropriate duration of the administration depend, in particular, on the species, age, sex, growth, and yield phase, state of health and nature of housing and feeding of the animals and can easily be determined by any expert.

The active compounds are administered to the animal by customary methods. The nature of the administration depends, in particular, on the species, behaviour and state of health of the animals.

The active compounds can be administered a single time. However, the active compounds can also be administered temporarily or continuously during the entire or during part of the growth and yield phase.

In the case of continuous administration, they can be used once or several times daily, at regular or irregular intervals.

Administration is oral or parenteral in formulations suitable for this or in the pure form.

The active compounds can be present in the formulations by themselves or as a mixture with other yield-promoting active compounds, mineral feedstuffs, trace element compounds, vitamins, non-protein compounds, dyestuffs, antioxidants, aroma substances, emulsifiers, flow control auxiliaries, preservatives and pressing auxiliaries.

Other yield-promoting active compounds are: for example antibiotics, such as tylosin and virginiamycin. Mineral feedstuffs are, for example, dicalcium phosphate, magnesium oxide and sodium chloride. Trace element compounds are, for example, iron fumarate, sodium iodide, cobalt chloride, copper sulphate and zinc oxide. Vitamins are, for example, vitamin A, vitamin $D_3$, vitamin E,B vitamins and vitamin C.

Non-protein compounds are, for example, biuret and urea. Dyestuffs are, for example, carotinoids, such as citranaxanthine, zeaxanthine and capsanthine.

Antioxidants are, for example, ethoxyquin and butyl-hydroxy-toluene.

Aroma substances are, for example, vanillin.

Emulsifiers are, for example, esters of lactic acid and lecithin.

Flow control auxiliaries are, for example, sodium stearate and calcium stearate.

Preservatives are, for example, citric acid and propionic acid.

Pressing auxiliaries are, for example, ligninsulphonates and cellulose ethers.

The active compounds can also be administered together with the feed and/or the drinking water.

Feed includes one-component feedstuffs of vegetable origin, such as hay, beet and cereal by-products, one-component feedstuffs of animal origin, such as meat, fats, milk products, bonemeal and fish products, and onecomponent feedstuffs such as vitamins, proteins, amino acids, for example DL-methionine, and salts, such as lime and sodium chloride, Feed also includes supplementary, prepared and mixed feedstuffs. These contain one-component feedstuffs in a composition which guarantees balanced nutrition in respect of the supply of energy and proteins and supply of vitamins, mineral salts and trace elements.

The concentration of the active compounds in the feed is usually about 0.01–500 ppm, preferably 0.1–50 ppm.

The active compounds can be added as such or in the form of premixes or feed concentrates to the feed.

An example of the composition of a chick-rearing feed containing the active compound according to the invention: 200 g of wheat, 340 g of corn, 361 g of shredded soy beans, 60 g of beef tallow, 15 g of dicalcium phosphate, 10 g of calcium carbonate, 4 g of iodinated sodium chloride, 7.5 g of a vitamin/mineral mixture and 2.5 g of an active compound premix give, after thorough mixing, 1 kg of feed.

One kg of feed mix contains: 600 international units of vitamin A, 100 international units of vitamin $D_3$, 10 mg of vitamin E, 1 mg of vitamin $K_3$, 3 mg of riboflavin, 2 mg of pyridoxine, 20 mcg of vitamin $B_{12}$, 5 mg of calcium pantothenate, 30 mg of nicotinic acid, 200 mg of choline chloride, 200 mg of $Mn\ SO_4 \times H_2O$, 140 mg of $Zn\ SO_4 \times 7\ H_2O$, 100 mg of $Fe\ SO_4 \times 7\ H_2O$ and 20 mg of $Cu\ SO_4 \times 5\ H_2O$.

2.5 g of active compound premix contain, for example, 10 mg of active compound, 1 g of DL methionine and soy bean flour as the remainder.

An example of the composition of a pig-rearing feed which contains an active compound according to the invention: 630 g of shredded feed cereal (composed of 200 g of corn, 150 g of shredded barley, 150 g of shredded oats and 130 g of shredded wheat), 80 g of fish meal, 60 g of shredded soy bean, 60 g of tapioca flour, 38 g of brewer's yeast, 50 g of vitamin/mineral mixture for pigs, 30 g of linseed cake meal, 30 g of corn gluten feed, 10 g of soy bean oil, 10 g of sugar cane molasses and 2 g of an active compound premix (composition, for example, as for the chick feed) give, after thorough mixing, 1 kg of feed.

The feed mixtures described are suitable for rearing and fattening, preferably, chicks and pigs respectively, but they can also be used in the same or a similar composition for feeding other animla.

EXAMPLE A

Rat feeding experiment

Female laboratory rats weighing 90–110 g of the SPF Wistar type (Züchtung Hagemann) are fed ad lib with standard rat food to which the desired amount of active compound is added. Each experiment is carried out with food from the same batch, so that differences in the composition of the food cannot impair the comparability of the results.

The rats receive water ad lib.

Each experimental group is formed by 12 rats which are fed with food to which the desired amount of active compound is added. A control group receives food without the active compound. The average body weight and the scatter in the body weight of the rats is the same in each experimental group, so that comparability of the experimental groups with one another is guaranteed.

During the 13-day experiment, the weight increase and food consumption are determined and the relative weight increase is calculated in comparison with the untreated control.

The results which can be seen from the table are obtained:

TABLE 1

| Rat feeding experiment | | |
|---|---|---|
| Active compound Example No. | Amount of Active compound used ppm | Relative weight increase % |
| 2 | 25 | 20 |
| 3 | 25 | 15 |
| 4 | 25 | 16 |
| 5 | 25 | 14 |
| 1 | 25 | 24 |
| 6 | 25 | 22 |
| 7 | 25 | 12 |
| 8 | 25 | 5 |
| 9 | 25 | 8 |
| 10 | 25 | 8 |

Examples of the process for the preparation of the compounds of the formula I

EXAMPLE 1

N-(2-(3,5-Dimethoxyphenyl)-2-hydroxyethyl)-N-2-(4-methoxyphenyl)-1-methylethyl)-hydroxylamine 250 mg (6.2 mmol) of NaBH$_4$ were introduced in portions into a solution of 1.1 g (3.1 mmol) of C-(3,5-dimethoxybenzoyl)-N-(2-(4-methoxyphenyl)-1-methylethyl)nitrone in 25 ml of absolute methanol, with cooling. the mixture was subsequently stirred at room temperature for 6 hours, acidified with dilute hydrochloric acid, with cooling, and evaporated. The aqueous residue was extracted with methylene chloride (3×10 ml) and the combined organic phases were dried over Na$_2$SO$_4$ and evaporated. 900 mg (73% of theory) of the hydrochloride of the title compound were obtained as an amorphous colorless powder. $^1$H-NMR (300 MHz, CDCL$_3$, δ (ppm)): 1.2 (d, 3H); 3.8 (s, 9H); 3.4–3.9 (m, 5H); 5.4 (m, 1H); 6.4 (t, 1H); 6.6 (dd, 2H); 6.8 (t, 2H); 7.1 (d, 2H).

The following compounds of the formula I were prepared analogously:

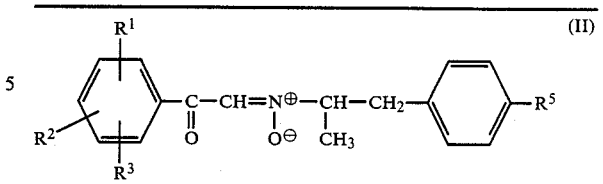

(II)

| Example No. | R$^1$ | R$^2$ | R$^5$ | Melting point [°C.] |
|---|---|---|---|---|
| $a$2 | H | 2-Cl | OCH$_3$ | oil |
| $a$3 | 3-CH$_3$SO$_2$CH$_2$ | 4-OH | OCH$_3$ | 67–68 |
| $a$4 | 3-CH$_3$O | 5-CH$_3$O | OCH$_3$ | 92–95 |
| $a$5 | 3-CH$_3$O | 4-CH$_3$O | OCH$_3$ | 134 |
| $a$6 | H | 3-Br | OCH$_2$COOCH$_3$ | 108–110 |
| $a$7 | H | 3-Br | COOCH$_3$ | 98–99 |
| $a$8 | 3-CH$_3$O | 4-CH$_3$O | COOCH$_3$ | 148 |

Examples of the process for the preparation of the compounds of the formula IV

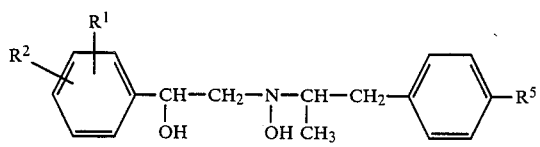

| Example No. | R$^1$ | R$^2$ | R$^5$ | Melting point [°C.] |
|---|---|---|---|---|
| 2 | H | 3-Br | OCH$_2$CH$_2$OH | amorphous |
| 3 | H | 3-Br | OCH$_3$ | 55–58° C. |
| 4 | H | 2-Cl | OCH$_3$ | amorphous |
| 5 | 3-CH$_3$SO$_2$CH$_2$ | 4-OH | OCH$_3$ | 60° C. |
| 6 | 3-CH$_3$O | 4-CH$_3$O | OCH$_3$ | amorphous |
| 7 | H | 3-Br | OCH$_2$COOC$_3$H$_z$ | amorphous |
| 8 | H | 3-Br | OCH$_2$COOCH$_3$ | amorphous |
| 9 | H | 3-Br | COOCH$_3$ | amorphous |
| 10 | 3-CH$_3$O | 4-CH$_3$O | COOCH$_3$ | amorphous |

Examples of the process for the preparation of the compounds of the formula II

EXAMPLE a1

C-(3-Bromobenzoyl)-N-(2-(4-methoxyphenyl)-1-methylethyl)nitrone 2.31 g (10 mmol) of 3-bromophenylglyoxal hydrate, 2.175 g (20 mmol) of N-(2-(4-methoxyphenyl)-1-methylethyl)hydroxylamine hydrochloride and 820 mg (10 mmol) of sodium acetate were stirred in 50 ml of absolute methanol at room temperature for 4 hours. After filtration, the fitrate was evaporated, 50 ml of water were added to the residue and the mixture was extracted with methylene chloride (3×25 ml).

The combined organic phases were dried over Na$_2$SO$_4$ and evaporated. The residue crystallized on trituration with n-pentane.

Yield: 2.9 g (77% of theory), melting point 98° C.

The following compounds of the formula II were prepared analogously:

EXAMPLE b1

N-(2-(4-Methoxyphenyl)-1-methylethyl)hydroxylamine hydrochloride 23.7 g (0.13 mol) of 4-methoxyphenylacetone oxime were dissolved in 200 ml of methanol and the solution was brought to pH 3 with dilute hydrochloric acid. 8.3 g (0.13 mol) of NaBH$_3$CN were then introduced in portions, the pH being kept at 3 by simultaneous addition of dilute hydrochloric acid. The mixture was subsequently stirred overnight at room temperature, the pH was brought to 1 with hydrochloric acid and the mixture was evaporated. The aqueous residue was extracted with methylene chloride (3×100 ml). The combined organic phases were washed with water (3×25 ml), dried over Na$_2$SO$_4$ and evaporated. Yield 23.3 g (80% of theory), melting point 124° C.

The following compounds of the formula IV were prepared analogously:

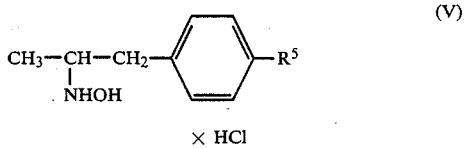

| Example No. | $R^5$ | Melting point [°C.] |
|---|---|---|
| $b_2$ | $OCH_2COOCH_3$ | oil |
| $b_3$ | $COOCH_3$ | oil |

It will be understood that the specification and examples are illustrative but not limitative of the present invention and that other embodiments within the spirit and scope of the invention will suggest themselves to those skilled in the art.

What is claimed is:

1. An arylethanolhydroxylamine of the formula

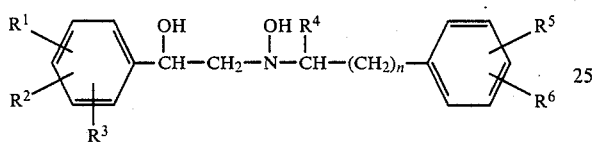

in which $R^1$ represents halogen, CN, $NO_2$, hydroxyl or optionally substituted alkyl, alkoxy or alkylthio, or furthermore represents alkoxycarbonyl or the radical $-NR^7R^8$, $R^2$ represents hydrogen, halogen, CN, hydroxyl or optionally substituted alkoxy, it being possible for the radicals $R^1$ and $R^2$, together with the adjacent C atoms, to form an optionally substituted dioxolanyl or dioxanyl ring, $R^3$ represents hydrogen or halogen, $R^4$ represents hydrogen or alkyl, $R^5$ represents hydrogen, optionally substituted alkyl or alkoxy, hydroxyl or halogen, $R^6$ represents acyl, acyloxy or alkoxy, which is optionally substituted, $R^7$ represents hydrogen or alkyl, $R^8$ represents hydrogen, alkyl, formyl (—CHO), acyl or optionally substituted aryl or aralkyl and n represents 0, 1 or 2, or a physiologically acceptable salt thereof.

2. A compound or salt according to claim 1, in which $R^1$ represents fluorine, chlorine, bromine, CN, nitro, hydroxyl, $C_{1-4}$-alkyl, $C_{1-4}$-halogenoalkyl, $C_{1-4}$-hydroxyalkyl, $C_{1-4}$-alkoxyalkyl, $C_{1-4}$-alkoxy, $C_{1-4}$-halogenoalkoxy, benzyloxy, $C_{1-4}$-alkylthio, $C_{1-4}$-halogenoalkylthio, $C_{1-4}$-alkoxycarbonyl, $C_{1-4}$-alkylsulphonylmethyl or the radical $-NR^7R^8$, $R^2$ represents hydrogen, fluorine, chlorine, bromine, CN, hydroxyl or $C_{1-4}$-alkoxy, it being possible for the radicals $R^1$ and $R^2$, together with the C atom to which they are bonded, to form a dioxolanyl or dioxanyl ring which is optionally substituted by fluorine or chlorine, $R^3$ represents hydrogen, fluorine, chlorine or bromine, $R^4$ represents hydrogen or $C_{1-3}$-alkyl, $R^5$ represents hydrogen, hydroxyl, fluorine, chlorine, bromine or $C_{1-10}$-alkyl, which is optionally substituted by halogen, OH, CN or phenyl, or represents $C_{1-4}$-alkoxy, $R^6$ represents $C_{1-3}$-alkoxy, which is optionally substituted by OH, halogen, $C_{1-2}$-alkoxy, $-COR^9$ or $-CONR^7R^8$, or represents one of the following radicals: $-COR^9$, $-SO_2R^{10}$, $-CONR^7R^8$ or $-O-COR^9$, $R^7$ represents hydrogen, $C_{1-4}$-alkyl, optionally substituted benzyl or phenyl, $R^8$ represents hydrogen, $C_{1-4}$-alkyl, —CHO, $-COR^9$, $-CONH_2$, $-CONH(C_{1-4}$-alkyl), $-CON(C_{1-4}$-alkyl)$_2$ or $-SO_2-(C_{1-4}$-alkyl), $R^9$ represents hydroxyl, $C_{1-4}$-alkoxy, $C_{1-4}$-alkyl or optionally substituted phenyl and $R^{10}$ represents $C_{1-4}$-alkyl or $C_{1-4}$-halogenoalkyl.

3. A compound or salt according to claim 1, in which $R^1$ represents chlorine, bromine, CN, OH, nitro, methyl, hydroxymethyl, methyl, methoxy, methylsulphonylmethyl, trifluoromethyl, amino, formamido, acetamido, methylsulphonamido, ureido or methoxybenzylamino, $R^2$ represents hydrogen, chlorine, bromine, CN, hydroxyl or methoxy, $R^3$ represents hydrogen, chlorine or bromine, $R^4$ represents hydrogen or methyl, $R^5$ represents hydrogen or methoxy or ethoxy, which are optionally substituted by OH, $R^6$ represents methoxy or ethoxy, which are optionally substituted by OH, or represents $-COR^9$ or $-O-CH_2-COR^9$, $R^9$ represents $C_{1-4}$-alkyl or $C_{1-4}$-alkoxy and n represents 1.

4. A compound or salt according to claim 1, in which $R^1$ represents chlorine, bromine, CN, OH, methylsulphonylmethyl, hydroxyl, methoxy or amino, $R^2$ represents hydrogen, chlorine, CN, hydroxyl or methoxy, $R^3$ represents hydrogen or chlorine, $R^4$ represents methyl, $R^5$ represents hydrogen, $R^6$ represents methoxy, hydroxyethyl or $-COR^9$ or $-O-CH_2COR^9$, $R^9$ represents methoxy or isopropoxy and n represents 1.

5. A compound according to claim 1, wherein such compound is N-(2-(3,5-dimethoxyphenyl)-2-hydroxyethyl)-N-2-(4-methoxy-phenyl)-1-methylethyl)-hydroxylamine of the formula

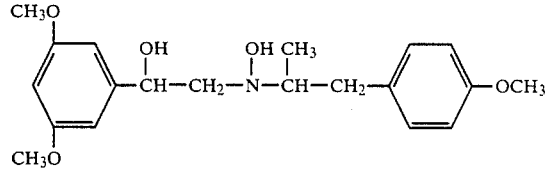

or a physiologically acceptable salt thereof.

6. A compound according to claim 1, wherein such compound is N-(2-(3-bromophenyl)-2-hydroxyethyl)-N-2-(4-hydroxyethyl-phenyl)-1-methylethyl)-hydroxylamine of the formula

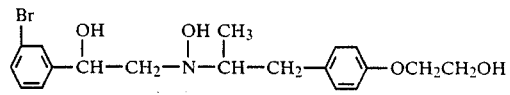

or a physiologically acceptable salt thereof.

7. A compound according to claim 1, wherein such compound is N-(2-(3-bromophenyl)-1-hydroxyethyl-N-2-(4-methoxy-phenyl)-1-methylethyl)-hydroxylamine of the formula

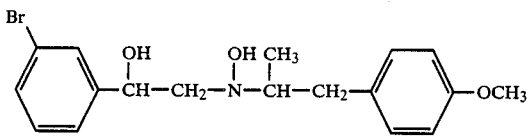

or a physiologically acceptable salt thereof.

8. A compound according to claim, wherein such compound is N-(2-(2-chlorophenyl)-2-hydroxyethyl)-N-2-(4-methoxy-phenyl)-1-methylethyl)-hydroxylamine of the formula

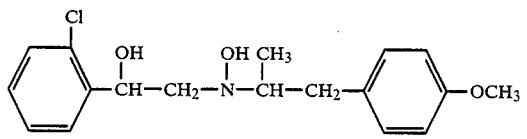

or a physiologically acceptable salt thereof.

9. A compound according to claim 1, wherein such compound is N-(2-(3,4-dimethoxyphenyl)-2-hydroxyethyl)-N-2-(4-methoxy-phenyl)-1-methylethyl)-hydroxylamine of the formula

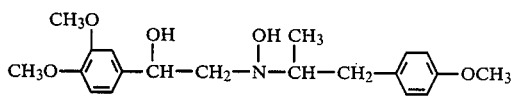

or a physiologically acceptable salt thereof.

10. An animal yield promoting composition comprising an amount effective therefor of a compound or salt according to claim 1 and a carrier.

11. A composition according to claim 10, wherein the carrier is an animal feed base.

12. A method of promoting the yield of animals which comprises administering to such animals a yield promoting effective amount of a compound or salt according to claim 1.

13. The method according to claim 12, wherein such compound is
N-(2-(3,5-dimethoxyphenyl)-2-hydroxyethyl)-N-2-(4-methoxy-phenyl)-1-methylethyl)-hydroxylamine,
N-(2-(3-bromophenyl)-2-hydroxyethyl)-N-2-(4-hydroxyethyl-phenyl)-1-methylethyl)-hydroxylamine,
N-(2-(3-bromophenyl)-2-hydroxyethyl)-N-2-(4-methoxy-phenyl)-1-methylethyl)-hydroxylamine,
N-(2-(2-chlorophenyl)-2-hydroxyethyl)-N-2-(4-methoxy-phenyl)-1-methylethyl)-hydroxylamine or
N-(2-(3,4-dimethoxyphenyl)-2-hydroxyethyl)-N-2-(4-methoxy-phenyl)-1-methylethyl)-hydroxylamine,
or a physiologically acceptable salt thereof.

* * * * *